US009050397B2

(12) United States Patent
Christiansen (10) Patent No.: US 9,050,397 B2
(45) Date of Patent: Jun. 9, 2015

(54) MEDICAL DELIVERY SYSTEM WITH A ROTATABLE CODING ELEMENT

(71) Applicant: Novo Nordisk A/S, Bagsvaerd (DK)

(72) Inventor: Asger Voss Christiansen, Guldborg (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 14/201,092

(22) Filed: Mar. 7, 2014

(65) Prior Publication Data

US 2014/0188051 A1 Jul. 3, 2014

Related U.S. Application Data

(63) Continuation of application No. 12/373,340, filed as application No. PCT/EP2007/057283 on Jul. 15, 2007, now Pat. No. 8,708,972.

(60) Provisional application No. 60/837,726, filed on Aug. 14, 2006.

(30) Foreign Application Priority Data

Jul. 15, 2006 (EP) .................................... 06014769
Aug. 14, 2006 (EP) .................................... 06118846

(51) Int. Cl.
*A61M 5/31* (2006.01)
*A61M 5/00* (2006.01)
(Continued)

(52) U.S. Cl.
CPC . *A61M 5/00* (2013.01); *A61M 5/24* (2013.01); *A61M 5/3135* (2013.01); *A61M 2005/2488* (2013.01); *A61M 2205/6045* (2013.01); *A61M 5/31535* (2013.01)

(58) Field of Classification Search
CPC ................... A61M 5/31535; A61M 5/31593; A61M 5/24; A61M 2005/2488; A61M 2205/6045
USPC .......................... 604/207, 208, 211, 224, 232
See application file for complete search history.

(56) References Cited

U.S. PATENT DOCUMENTS 1,594,493 A 8/1926 Brown
2,020,828 A 11/1935 Goldberg
(Continued)

FOREIGN PATENT DOCUMENTS

CH 0315980 A 9/1956
CH 0501411 A 1/1971
(Continued)

OTHER PUBLICATIONS

English Language Abstract of German Patent Publication DE20110690, published Sep. 13, 2001.
(Continued)

*Primary Examiner* — Nicholas Lucchesi
*Assistant Examiner* — Gerald Landry, II
(74) *Attorney, Agent, or Firm* — Wesley A. Nicolas; Richard W. Bork; Reza Green (57) ABSTRACT

A medical delivery system having a container and a dosing assembly, and wherein one of the container and the dosing assembly comprises a rotatable element adapted to engage the other one of the container and the dosing assembly.
A container suitable for use in said medical delivery system.
A dosing assembly suitable for use in said medical delivery system.

14 Claims, 7 Drawing Sheets

(51) Int. Cl.
*A61M 5/24* (2006.01)
*A61M 5/315* (2006.01)

(56) References Cited

U.S. PATENT DOCUMENTS

| | | | |
|---|---|---|---|
| 2,392,196 A | 1/1946 | Smith | |
| 2,707,466 A | 5/1955 | Hoskins et al. | |
| 2,818,864 A | 1/1958 | Hudson | |
| 2,865,372 A | 12/1958 | Miskel et al. | |
| 2,880,723 A | 4/1959 | Adams | |
| 2,888,924 A | 6/1959 | Dunmire | |
| 2,956,563 A | 10/1960 | Sarnoff | |
| 3,021,840 A | 2/1962 | Hallamore et al. | |
| 3,115,135 A | 12/1963 | Sarnoff | |
| 3,130,724 A | 4/1964 | Higgins et al. | |
| 3,130,742 A | 4/1964 | Higgins et al. | |
| 3,144,178 A | 8/1964 | Sarnoff et al. | |
| 3,170,667 A | 2/1965 | Szohatzky | |
| 3,336,924 A | 8/1967 | Sarnoff et al. | |
| 3,375,825 A | 4/1968 | Keller | |
| 3,556,099 A | 1/1971 | Knight et al. | |
| 3,820,652 A | 6/1974 | Thackston | |
| 3,831,599 A | 8/1974 | Needham | |
| 3,880,162 A | 4/1975 | Simmons | |
| 3,895,633 A | 7/1975 | Bartner et al. | |
| 3,916,893 A | 11/1975 | De Felice | |
| 3,989,044 A | 11/1976 | Meierhoefer | |
| 4,089,432 A | 5/1978 | Crankshaw et al. | |
| 4,150,673 A | 4/1979 | Watt | |
| 4,280,723 A | 7/1981 | Moldestad | |
| 4,314,556 A | 2/1982 | Ma | |
| 4,490,142 A | 12/1984 | Silvern | |
| RE31,873 E | 4/1985 | Howes | |
| RE31,878 E | 5/1985 | Ritsema | |
| 4,592,745 A | 6/1986 | Rex et al. | |
| 4,619,640 A | 10/1986 | Potolsky et al. | |
| 4,619,651 A | 10/1986 | Kopfer et al. | |
| 4,664,656 A | 5/1987 | Taddei | |
| 4,685,314 A | 8/1987 | Greenwalt et al. | |
| 4,693,833 A | 9/1987 | Toshikuni et al. | |
| 4,740,205 A | 4/1988 | Seltzer et al. | |
| 4,768,568 A | 9/1988 | Fournier et al. | |
| 4,781,701 A | 11/1988 | Geprags | |
| 4,944,736 A | 7/1990 | Holtz | |
| 4,948,000 A | 8/1990 | Grabenkort | |
| 4,973,318 A | 11/1990 | Holm et al. | |
| 4,976,701 A | 12/1990 | Ejlersen et al. | |
| 5,000,744 A | 3/1991 | Hoffman et al. | |
| 5,002,537 A | 3/1991 | Hoffman et al. | |
| 5,017,190 A | 5/1991 | Simon et al. | |
| 5,078,698 A | 1/1992 | Stiehl et al. | |
| 5,084,017 A | 1/1992 | Maffetone | |
| 5,205,833 A | 4/1993 | Harsh et al. | |
| 5,226,896 A | 7/1993 | Harris | |
| 5,244,465 A | 9/1993 | Michel | |
| 5,269,317 A | 12/1993 | Bennett | |
| 5,286,258 A | 2/1994 | Haber et al. | |
| 5,458,580 A | 10/1995 | Hajishoreh | |
| 5,478,323 A | 12/1995 | Westwood et al. | |
| 5,496,286 A | 3/1996 | Stiehl et al. | |
| 5,498,253 A | 3/1996 | Aswad et al. | |
| 5,554,134 A | 9/1996 | Bonnichsen | |
| 5,584,815 A | 12/1996 | Pawelka et al. | |
| 5,611,783 A * | 3/1997 | Mikkelsen | 604/208 |
| 5,693,027 A | 12/1997 | Hansen et al. | |
| 5,743,889 A | 4/1998 | Sams | |
| 5,938,642 A | 8/1999 | Burroughs et al. | |
| 5,954,700 A | 9/1999 | Kovelman | |
| 5,957,896 A * | 9/1999 | Bendek et al. | 604/207 |
| 6,017,330 A | 1/2000 | Hitchins et al. | |
| 6,036,675 A | 3/2000 | Thorne et al. | |
| 6,197,040 B1 | 3/2001 | LeVaughn et al. | |
| 6,582,399 B1 | 6/2003 | Smith et al. | |
| 6,582,408 B1 | 6/2003 | Buch-Rasmussen et al. | |
| 6,648,859 B2 * | 11/2003 | Bitdinger et al. | 604/232 |
| 6,752,798 B2 | 6/2004 | McWethy et al. | |
| 7,604,619 B2 | 10/2009 | Eich et al. | |
| 2001/0047153 A1 | 11/2001 | Trocki et al. | |
| 2002/0016571 A1 | 2/2002 | Kirchhofer et al. | |
| 2002/0099360 A1 | 7/2002 | Bierman | |
| 2002/0169470 A1 | 11/2002 | Kuhr et al. | |
| 2003/0004466 A1 | 1/2003 | Bitdinger et al. | |
| 2003/0078195 A1 * | 4/2003 | Kristensen et al. | 514/3 |
| 2004/0210199 A1 | 10/2004 | Atterbury et al. | |
| 2004/0215152 A1 | 10/2004 | Kirchhofer et al. | |
| 2004/0238776 A1 | 12/2004 | Peters et al. | |
| 2005/0033224 A1 * | 2/2005 | Kirchhofer et al. | 604/68 |
| 2005/0137571 A1 * | 6/2005 | Hommann | 604/500 |
| 2006/0153693 A1 * | 7/2006 | Fiechter et al. | 417/63 |
| 2007/0088288 A1 * | 4/2007 | Barron et al. | 604/207 |
| 2008/0047550 A2 * | 2/2008 | Steiner et al. | 128/200.23 |
| 2008/0051713 A1 | 2/2008 | Kohlbrenner et al. | |
| 2009/0054851 A1 * | 2/2009 | Radmer et al. | 604/211 |
| 2010/0004603 A1 | 1/2010 | Kristensen et al. | |
| 2010/0030158 A1 | 2/2010 | Christiansen | |
| 2011/0054412 A1 | 3/2011 | Eich et al. | |

FOREIGN PATENT DOCUMENTS

| | | |
|---|---|---|
| DE | 2137405 A1 | 2/1973 |
| DE | 4419235 A1 | 12/1995 |
| DE | 20110690 U1 | 9/2001 |
| EP | 217055 A1 | 4/1987 |
| EP | 549694 | 7/1993 |
| EP | 513128 | 7/1995 |
| EP | 762311 A2 | 3/1997 |
| EP | 774270 A1 | 5/1997 |
| EP | 832661 A2 | 4/1998 |
| EP | 897728 | 2/1999 |
| EP | 897729 A2 | 2/1999 |
| GB | 301961 A | 12/1928 |
| GB | 1205201 A | 9/1970 |
| GB | 1437595 A | 5/1976 |
| GB | 1525455 A | 9/1978 |
| GB | 2214819 A | 9/1989 |
| WO | 89/02760 A1 | 4/1989 |
| WO | 90/09202 | 8/1990 |
| WO | 9110460 A1 | 7/1991 |
| WO | 92/04926 A1 | 4/1992 |
| WO | 9707841 | 3/1997 |
| WO | 98/47559 A1 | 10/1998 |
| WO | 98/56438 A1 | 12/1998 |
| WO | 00/02605 A1 | 1/2000 |
| WO | 00/35519 A1 | 6/2000 |
| WO | 0172361 | 10/2001 |
| WO | 02/30490 A2 | 4/2002 |
| WO | 03/011372 A2 | 2/2003 |
| WO | 03/011373 A1 | 2/2003 |
| WO | 03/017915 A1 | 3/2003 |
| WO | 03097131 A1 | 11/2003 |
| WO | 2006/069456 A1 | 7/2006 |
| WO | 2008/009646 A1 | 1/2008 |
| WO | 2012/152667 A1 | 11/2012 |

OTHER PUBLICATIONS

Novo Nordisk Product Brochure for Insuject-X 1987.
English Language Abstract for CH0315980.
English Language Abstract for CH0501411.
English Language Abstract for DE2137405.
English Language Abstract for DE4419235.
Non-Final Office Action Mailed Apr. 9, 2004 in U.S. Appl. No. 10/230,428, filed Aug. 23, 2002; First Named Inventor: Kristensen.
Non-Final Office Action Mailed Nov. 18, 2004 in U.S. Appl. No. 10/230,428, filed Aug. 23, 2002; First Named Inventor: Kristensen.
Notice of Allowance Mailed May 19, 2005 in U.S. Appl. No. 10/230,428, filed Aug. 23, 2002; First Named Inventor: Kristensen.
Non-Final Office Action Mailed Feb. 9, 2006 in U.S. Appl. No. 10/230,428, filed Aug. 23, 2002; First Named Inventor: Kristensen.
Notice of Allowance Mailed Oct. 10, 2006 in U.S. Appl. No. 10/230,428, filed Aug. 23, 2002; First Named Inventor: Kristensen.
Non-Final Office Action mailed Dec. 12, 2006 in U.S. Appl. No. 10/230,428, filed Aug. 23, 2002; First Named Inventor: Kristensen.

(56) References Cited

OTHER PUBLICATIONS

Non-Final Office Action Mailed Feb. 10, 2009 in U.S. Appl. No. 11/784,738, filed Apr. 9, 2007; First Named Inventor Kristensen.
Final Office Action Mailed Jun. 2, 2009 in U.S. Appl. No. 11/784,738, filed Apr. 9, 2007; First Named Inventor Kristensen.
Final Office Action Mailed Aug. 12, 2010 in U.S. Appl. No. 12/522,566, filed Sep. 2, 2009; First Named Inventor: Kristensen.
Notice of Allowance Mailed Dec. 13, 2010 in U.S. Appl. No. 12/522,566, filed Sep. 2, 2009; First Named Inventor: Kristensen.
Non-Final Office Action Mailed Oct. 29, 2010 in U.S. Appl. No. 12/305,684, filed Dec. 19, 2008; First Named Inventor: Steenfeldt-Jensen.
Non-Final Office Action Mailed Jan. 19, 2010 in U.S. Appl. No. 12/373,339, filed Jan. 12, 2009 by Hansen.
Final Action Mailed Jul. 30, 2010 in U.S. Appl. No. 12/373,339, filed Jan. 12, 2009 by Hansen.
Non-Final Office Action Mailed Nov. 24, 2010 in U.S. Appl. No. 12/373,339, filed Jan. 12, 2009 by Hansen.
Non-Final Office Action Mailed Feb. 17, 2011 in U.S. Appl. No. 12/357,013, filed Jan. 21, 2009 by Christiansen.
Non-Final Office Action Mailed Feb. 1, 2010 in U.S. Appl. No. 12/374,600, filed Jan. 21, 2009 by Christiansen.
Non-Final Office Action Mailed Feb. 18, 2011 in U.S. Appl. No. 12/373,340, filed Jan. 12, 2009 by Christiansen.
Final Office Action Mailed Jul. 15, 2010 in U.S. Appl. No. 12/374,600, filed Jan. 21, 2009 by Christiansen.
Non-Final Office Action Mailed Mar. 4, 2011 in U.S. Appl. No. 12/374,600, filed Jan. 21, 2009 by Christiansen.
Search Report from International Application No. PCT/EP2007/062661, mailed Feb. 25, 2008.
English language translation for DE20110690.
English language translation for DE2137405.
English language translation for DE4419235.
English language translation for CH0315980.
English language translation for CH0501411.
English Abstract of DE 20110690 Published Sep. 13, 2001.

* cited by examiner

MEDICAL DELIVERY SYSTEM WITH A ROTATABLE CODING ELEMENT

CROSS-REFERENCE TO RELATED APPLICATIONS

This application is a continuation of U.S. application Ser. No. 12/373,340, filed Feb. 20, 2009, which is a 35 U.S.C. §371 national stage application of International Patent Application PCT/EP2007/057283 (published as WO 2008/009646), filed Jul. 15, 2007, which claimed priority of European Patent Applications 06014769.1, filed Jul. 15, 2006, and 06118846.2, filed Aug. 14, 2006; this application further claims priority under 35 U.S.C. §119 of U.S. Provisional Application 60/837,726, filed Aug. 14, 2006, incorporated herein by reference.

FIELD OF THE INVENTION

The present invention relates to a medical delivery system comprising a container and a dosing assembly. In particular the present invention relates to medical delivery system wherein one of the container and the dosing assembly comprises a rotatable element adapted to engage the other one of the container and the dosing assembly. Furthermore, the present invention relates to a container and a dosing assembly each of which are suitable for use in the medical delivery system according to the present invention.

BACKGROUND OF THE INVENTION

Generally, in order to provide superior medication delivery devices which are likely to be well received by particular groups of patients, a greater diversity in drug delivery systems have been launched to the benefit of patients. As the number of commercially available delivery systems increase, numerous different types of medication holding cartridges or containers are distributed. Most of these types of containers differ in various aspects.

Each medicament container may be filled with a particular type of medicament selected from a large variety of different medicaments, but also different kinds of the same class of medicament (e.g. rapid or long acting insulin) and different concentrations of each particular medicament may be accommodated in the containers.

Moreover, different container volumes may be introduced in order to customize each container, and, thus, the delivery system to the needs of particular users. Variation of container volume may be provided by changing the length or diameter of the container. These modifications usually imply corresponding modifications of the dosing assembly of a medication delivery system, so as to provide a particular stroke of a driving element for expelling the medicament from the container or to provide optimal dosing precision. Further discrimination between different medicament containers may be occasioned by the design requirements for each particular delivery system, such as required sliding friction of the piston accommodated in the container.

In order to discriminate between a larger variety of available containers, numerous container coding systems have been developed which primarily relies on the electronic reading and recognition of specific containers in order to allow delivery of a specific type of a medicament by a dedicated delivery device. The following mechanical coding systems are known in the art:

U.S. Pat. No. 5,611,783 relates to a pen shaped syringe comprising a distal part which may comprise an ampoule and a proximal part containing a dose setting and drive mechanism. The proximal and distal parts have interlocking bayonet coupling means. Protrusions may be provided to form a pattern ensuring that a certain distal part may only be used in connection with a certain proximal part.

WO 03/017915 A1 discloses a cartridge having a distal end provided with a mechanical coding. The mechanical coding has the form of a circular protrusion where the circular outer diameter is dedicated a specific concentration of insulin contained in the cartridge.

U.S. Pat. No. 5,693,027 discloses a plastic top for adapting a standard cartridge to a chosen syringe. The plastic top may be provided with means for keyed engagement with corresponding means in a syringe to keep it unrotable when mounted with a cartridge in the syringe. In some types of syringes such keyed engagement between cartridge and syringe is further used to ensure that only a certain type of cartridge is used.

U.S. Pat. No. 6,648,859 B2 discloses a drug cartridge assembly for use with a reuseable pen body assembly of a medication delivery pen. In order to eliminate cross-use the pen body assembly and the drug cartridge are keyed i.e. they may be threadedly engaged by corresponding threads and grooves, bayonet threads, and grooves, snap fits or a pair of lugs that mate in reverse Luer-Lock manner. The mating members are selected so as to prevent cross-use with other assemblies, e.g., the pitch of the threads may be angled so as to mate only with one another and not with other assemblies.

Yet another prior art system is described in DE 201 10 690.

It is an object of a preferred embodiment of the present invention to provide an alternative to the known systems. Furthermore, it is an object of a preferred embodiment of the present invention to provide a medication delivery system with a large number of possible coding geometries.

Furthermore, it is an object of a preferred embodiment of the present invention to provide a coding system wherein the user experiences substantially the same operational fastening movement when the container and dosing assembly of a predetermined medical delivery system are coupled/uncoupled to each other regardless of the specific choice among sets of compatible container/dosing assemblies. Additionally, it is an object of a preferred embodiment of the present invention to provide a system having a large number of differently coded containers/dosing assemblies while simultaneously obtaining a rugged system where the possibility of mechanical failure is minimized Furthermore, it is an object of a preferred embodiment of the present invention to provide an intuitive fastening mechanism for fastening the container to the dosing assembly.

BRIEF DESCRIPTION OF THE INVENTION

In a FIRST aspect the present invention relates to a medical delivery system comprising:
- a container adapted to contain a medicament in a chamber defined by the container and a slidably arranged piston which is moveable in a distal direction towards an outlet so as to reduce the volume of the chamber and expel the medicament through the outlet;
- a dosing assembly adapted to be fastened to the container, so as to allow a driver of the dosing assembly to move the piston of the container in the distal direction;
- wherein the dosing assembly defines a first fastening means which during fastening of the container to the dosing assembly engages a second fastening means of the container whereby the container is fastened to the dosing assembly through a predetermined movement defined by at least one of the first and the second fastening means, the predetermined movement being less than one revolution;

wherein one of the container and the dosing assembly defines a first part comprising a rotatable element defining one or more protrusion(s) and/or indentation(s) which during fastening of the container to the dosing assembly are adapted to be received in/by one or more corresponding indentation(s) and/or protrusion(s) of a second part which is defined by the other one of the container and the dosing assembly, and wherein the rotatable element is adapted to rotate about a longitudinal axis of and relative to the first part during fastening of the container to the dosing assembly.

By varying the rotational position of the rotatable element in different medical delivery systems according to the present invention, it may be ensured that a container of a first medical delivery system is coded such that it cannot be fastened to a dosing assembly of a second medical delivery system. Analogously, it may be ensured that the container of the second medical delivery system is coded such that it cannot be fastened to the dosing assembly of the first medical delivery system. Accordingly, the medical system according to the present invention improves user safety as only predetermined containers may be attached to a specific dosing assembly. Thus, the dosing assembly may be designated to be used with a predetermined kind and/or concentration of a medicament and containers accommodating other concentrations or types of medicaments cannot be attached to the dosing assembly.

The system according to the present invention provides the advantage that the devices may be coded by varying the rotational position of the rotatable element. This is advantageous from a manufacturing point of view, as the same tools used for manufacturing a container, a dosing assembly and a rotatable element may result in a plurality of different containers and dosing assemblies which have been coded differently.

In the context of the present invention the term "medical delivery system" shall be understood as any system capable of administering a medicament-containing flowable drug. Examples of medical delivery systems are infusion pump applications, dosers, pen-shaped dosers, motor-dosers, and automated syringes such as the AutoPen™.

The invention is applicable to all kinds of medicament delivery devices capable of delivering a medicament to a user from a container which is adapted to be coupled to a dosing assembly of the delivery device. The delivery device may include any delivery device for transcutaneous, subcutaneous, intravenous, intra muscular or pulmonary administration of a drug.

As used herein, the term "medicament" is meant to encompass any medicament-containing flowable drug capable of being passed through a delivery means such as a hollow needle in a controlled manner, such as a liquid, solution, gel or fine suspension. Representative medicaments includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

The chamber of the container may defined by one or more sidewalls of the container and the slidably arranged piston. In most embodiments at least a part of the container is ring-shaped and defines a cylindrical cavity in which the piston is received. The distal end of the container may comprise a seal for penetration by a cannula so as to allow a medicament contained in the chamber to be expelled through the cannula.

The distal end of the container may be adapted to be attached to a holder holding a cannula. As an example the distal end of the container may comprise a thread adapted to cooperate with a corresponding thread of the holder so as to allow the holder to be screwed onto the container.

The outlet of the container may be adapted to cooperate with or be defined by a cannula or a needle or a needle hub or an infusion set, or any other fluid communicating conduit adapted to provide fluid access to a medicament accommodated in the container.

The driver of the dosing assembly may comprise a piston rod adapted to move the piston in the distal direction. The piston rod may comprise an element which is more rigid than the piston and is adapted to abut at least a part of and preferably most of the proximal facing surface of the piston whereby a force applied by the piston rod to the rigid element is applied to a larger area of the proximal surface of the piston than if the piston rod had engaged the piston directly.

The dosing assembly defines a first fastening means which during fastening of the container to the dosing assembly engages a second fastening means of the container. In one embodiment a proximal facing surface of the first fastening means of the dosing assembly engages a distal facing surface of the second fastening means of the container.

The container may be fastened to the dosing assembly through a predetermined movement comprising at least a concurrent axial and rotational movement, such as a helical movement. The rotational movement incurred by the concurrent axial and rotational movement is less than one revolution, such as less than 120 degrees, such as less than 90 degrees, such as less than 60 degrees. When the proximal facing surface of the first fastening means and the distal facing surface of the second fastening means are brought into engagement, rotation of the container relative to the dosing assembly may cause the container and the dosing assembly to be pulled towards each other.

In a first embodiment the first fastening means of the dosing assembly defines a groove adapted to receive a projection defined by the second fastening means of the container. During fastening of the container to the dosing assembly, a substantially proximal facing surface of the first fastening means of the dosing assembly engages a substantially distal facing surface of the container. The predetermined movement is defined by the shape of at least one of the engaging surfaces. In a further embodiment the second fastening means defines a plurality of projections such as two, three or four, and the first fastening means defines a corresponding plurality of grooves adapted to be engaged by the projections.

In a second embodiment the groove(s) is/are defined by the container and the projection(s) is/are defined by the dosing assembly. In a third embodiment the container defines a combination of grooves and projections adapted to be engaged by corresponding projections and grooves defined by the dosing assembly.

In the context of the present invention the terms "groove" and "projection" are only used in connection with the first and second fastening means, and "indentation" and "protrusion" are only used in connection with engaging/receiving mechanism of the rotatable element and the second part extending coding mechanism. However, "groove" and "indentation" shall be seen as synonyms and "protrusion" and "projection" shall be seen as synonyms.

In one embodiment the rotatable element defines one or more protrusions (such as two, three, four or five) each of which is adapted to engage a corresponding/mating/matching indentation of the second part. In a second embodiment the rotatable element defines one or more indentations (such as two, three, four or five) each of which is adapted to engage a corresponding/mating/matching protrusion of the second part. In a third embodiment the rotatable element comprises one or more protrusions and one or more indentations. In the latter embodiment, the protrusion(s) of the rotatable element is/are adapted to engage one or more indentations of the second part and the indentation(s) is/are adapted to engage one or more protrusions of the second part.

In one embodiment the indentations are wider (circumferentially) than the protrusions, and, thus, the projections are allowed to move rotationally inside the indentations, whereby the second part will be allowed to rotate relative to the rotatable element when the protrusions are received in the indentations. The possible relative rotation between the second part and the rotatable element may be less than 60 degrees about the longitudinal axis of the device, such as less than 45 degrees, such as less than 30 degrees, such as less than 5 degrees, such as less than 1 degree. In another embodiment the possible relative rotation between the rotatable element and the first part is 40-100 percent of the relative rotation between the second part and the first part during fastening of the container to the dosing assembly, such as 60-100 percent, such as 80-100 percent.

The sidewalls of the protrusions may be v-shaped i.e. the width of the sidewall may decrease in the axial direction. Similarly, the indentations may be v-shaped.

The protrusion(s) and the indentation(s) may have substantially the same circumferential width. Alternatively, the protrusion may be slightly wider than the indentation and at least one of the protrusion and the indentation may be made of a resilient material.

In one embodiment the rotatable element is locked for rotation relative to the second part during fastening of the container to the dosing assembly, e.g. the possible relative rotation between the rotatable element and the second part is less than 1 degree.

Furthermore, when the container comprises one or more axially extending indentations, the second fastening means may be axially positioned between the distal most surface of at least one of the one or more indentations (i.e. a bottom surface of the indentation), and the proximal end surface of the container.

In one embodiment the first and second fastening means, and the protrusions and the indentations are arranged such that first and second fastening means must at least partly engage in order for the protrusion to be received in the indentation. In other words when fastening the container to the dosing assembly, the protrusion(s) cannot be received in the indentation(s), if not the projection(s) (of the first or second fastening means) are at least partly received in the groove(s) (of the first or second fastening means). Accordingly, the medical device cannot be uncoded by advancing at least a part of the protrusions into the indentations and rotating the rotatable element relative to the first part until the projections could be received in the grooves, whereby the container could be fastened to the dosing assembly.

The rotatable element is adapted to rotate about the longitudinal axis (the centre axis) of the first part and may in some embodiments be locked for axial movement relative to the first part.

In one embodiment the rotation of the rotatable element relative to the first element is a combined rotational and radial movement. In a particular embodiment the rotatable element is moved along a line defining a tangent to a circle, the centre of which coincides with the longitudinal axis (the centre axis) of the device, when the container is fastened to the dosing assembly.

In one embodiment the rotatable element is adapted to be changed between a first and a second rotational position relative to the first part such that prior to fastening of the container to the dosing assembly, the rotatable element is positioned in the first position and when the container is fastened to the dosing assembly the rotatable element is positioned in the second position. In one embodiment the rotatable element is biased towards the first position e.g. by means of a spring.

In one embodiment the dosing assembly defines the first part and thus comprises the rotatable element. In the latter embodiment the rotatable element may be provided on an outer surface of the dosing assembly. Alternatively, the rotatable element may be provided on an inner surface of the dosing assembly.

In an alternative embodiment the container defines the first part and comprises the rotatable element. Again, the rotatable element may be provided on the inner or outer surface of the container.

The protrusions and/or indentation may extend in a substantially axial and/or radial direction of the device. The rotatable element may be a ring-shaped element. The rotatable element may be made of a wire or a piece of sheet metal. The wire and the sheet metal may be bent e.g. by means of a punching apparatus, so as to define the protrusions or indentations. In an alternative embodiment the rotatable element is made of a moulded metal and/or plastic material such as Poly-propen, Poly-carbonat, Poly-oxymethylen. Alternatively, the rotatable element is made by means of a 3d-printing printing process.

In one embodiment the ring-shaped element comprises at least one protrusion and is adapted to contract radially upon advancement of each of the at least one protrusion into the corresponding indentation of the second part. When the ring-shaped element contracts the diameter decreases. Accordingly, in one embodiment the ring-shaped element may abut a surface of the first part prior to advancement of the at least one protrusion into the corresponding indentation of the second part, whereby the ring-shaped element may be rotationally and/or axially retained relative to the first part. When the one or more projections have been advanced into the mating indentations, the ring-shaped element have contracted and is thus not retained relative to the first member as the ring-shaped element no longer abut the ring-shaped element.

In order to provide the contracting effect one or more of the at least one protrusion of the ring-shaped element may be v-shaped and the widest part of the v-shaped part may be wider than the widest part of the matching indentation. Accordingly, when the v-shaped protrusion is forced into the indentation, the sides of the v-shaped protrusion are forced towards each other whereby the ring-shaped element contracts. By providing a ring-shaped element which abut the first part when the container is not fastened to the dosing assembly, it may be ensured that the ring-shaped element will not change rotational position. If the ring-shaped element could change position when the container is not fastened to the dosing assembly, it would not be possible to fasten a predetermined container to a dosing assembly.

Alternatively, or as a supplement, the ring-shaped element may comprise at least one protrusion and may be adapted to expand radially upon advancement of each of the at least one protrusion into the corresponding indentation of the second part. When the ring-shaped element expands, the diameter of the ring-shaped element increases. The expanding effect may be achieved by providing a protrusion defining a loop as will be described in further detail below in relation to the figures.

Moreover, the rotatable element may be retained in relation to the first part by providing at least one radially extending knob on the rotatable element, which knob upon radial contraction or expansion of the rotatable element engages or disengages a depression defined in the first part, whereby the rotatable element is unlocked/locked from the first part and allowed to or prevented from rotate(ing) about a center axis of and relative to the first part. The depression may be defined by two adjacent radially extending knobs between which the depression is defined.

Alternatively, rotatable element may comprise a v-shaped protrusion and a loop-shaped protrusion, whereby advancement of the rotatable element into matching indentations, causes the v-shaped protrusion to contract and the loop-shaped protrusion to expand whereby a knob provided between the two protrusions is caused to rotate. This may be used to rotate the knob out of engagement of a depression.

In order to provide a system wherein the rotational position of the rotatable element defines the coding of the first part, the first part may be adapted to retain the rotatable element in a plurality of predetermined positions. Accordingly during manufacturing the first part, said first part may be coded by choosing a desired rotational position of the rotatable part relative to the first part. This provides the advantage that with the same two elements (the rotatable element and the first part) a plurality of different codes may be achieved.

In one embodiment the container comprises a cartridge holder and a cartridge defining said chamber. The second fastening means may be defined by or attached to the cartridge holder. Moreover, the indentation(s)/protrusion(s) may be defined by the cartridge holder. The cartridge and the cartridge holder may be two separate elements, and the cartridge may be frictionally retained in the cartridge holder. In one embodiment the cartridge is made of glass and the cartridge holder is made of a non-glass material for protecting the glass cartridge. The cartridge may be non-removably retained in the cartridge holder, such that if the cartridge is removed from the cartridge holder it cannot be reattached by hand and without tools. This provides the advantage that the cartridge holder cannot be reused when the cartridge has been emptied, accordingly a cartridge with a wrong medicament cannot be inserted into the cartridge holder and be dispensed by use of the dosing assembly. The cartridge holder and the cartridge may define a monolithic element, i.e. forming a one element without seams. Such a monolithic element may be formed as a molded article made of a synthetic resin such as Topas® or polypropylene. Such a molded article may include the fastening and coding elements which are formed during molding. However, any material which is suitable for long-term storage of the specific medication to be accommodated in the container may be used.

As describe in above at least a part of said predetermined movement may be a concurrent axial and rotational movement. Moreover, at least one of:
the first and second fastening means, and
the protrusion(s) and/or indentation(s) of each of the rotatable element and the second part, may be adapted to prevent a part of the axial and/or rotational movement of the predetermined movement, so as to prevent coupling of the container to the dosing assembly, unless:
each of the first and second fastening means defines a predetermined coding geometry, and/or
each of the protrusion(s) and/or indentation(s) of each of the rotatable element and the second part defines a predetermined coding geometry, and/or
the rotatable element is positioned in a predetermined rotational position relative to the first part.

Moreover, the coding geometry of:
one or more of the first and/or second fastening means, and/or
one or more of the protrusion(s) and/or indentation(s) of at least one of the rotatable element and the second part,
may be defined by at least one of: a circumferential extent of the first and second fastening means, an axial extent of the first and second fastening means, a radial extent of the first and second fastening means and the circumferential position of the first and second fastening means.

Accordingly, it will be appreciated that the medical delivery system according to the present invention provides a plurality of coding geometries each of which may be used to designate different features. As an example the first and second fastening means may be used to designate a first predetermined feature of the medicament such as its kind, and the rotational position of the rotatable element may be used to designate a second predetermined feature of the medicament such as its concentration. Other examples of features which may be designated by a coding geometry are: male/female medication; child/adult medication; prophylactic/therapeutic medication, slow/fast acting medication.

Alternatively, the first and second fastening means, and the rotational position of the rotatable element may be redundant such that if one of them fails, the other one will ensure that only predetermined containers and dosing assemblies can be fastened to each other. Accordingly, an extra level of security is provided due to the two redundant coding geometries.

One embodiment comprises:
a first container having any of the abovementioned features and/or elements, which first container is adapted to be fastened to a first dosing assembly having any of the abovementioned features and/or elements; and
a second container having any of the abovementioned features and/or elements, which second container is adapted to be fastened to a second dosing assembly having any of the abovementioned features and/or elements; and
wherein at least one of:
the first fastening means of the dosing assemblies,
the second fastening means of the containers, and
each of the protrusion(s) and/or indentation(s) of the rotatable elements and the second parts,
are adapted to prevent the first dosing assembly and second container from being fastened to each other, and to prevent the second dosing assembly and the first container from being fastened to each other.

Moreover, the predetermined movement required for coupling and uncoupling the first container to the first dosing assembly and for coupling the second container to the second dosing assembly may be essentially the same.

In a SECOND aspect the present invention relates to a container suitable for use (adapted to be used) in a medical delivery system according to the first aspect of the invention.

It will be appreciated that the invention according to the second aspect may comprise any feature and/or element of the invention according to the first aspect. In particular the container of the second aspect may comprise any feature and/or element of the container according to the first aspect of the invention.

In a THIRD aspect the present invention relates to a dosing assembly suitable for use (adapted to be used) in a medical delivery system according to the first aspect of the invention.

It will be appreciated that the invention according to the third aspect may comprise any feature and/or element of the invention according to the first aspect. In particular the dosing assembly of the third aspect may comprise any feature and/or element of the dosing assembly according to the first aspect of the invention.

DETAILED DESCRIPTION OF THE INVENTION

The invention will now be described in further detail with reference to the drawings in which:

FIGS. 1, 3 and 4 disclose different embodiments of the medical delivery system according to the present invention, FIG. 2 discloses a protrusion of a rotatable ring, FIGS. 5 and 6 disclose a longitudinal cross-section of a rotatable ring received in a first part, FIGS. 7-12 disclose isometric drawings and a cross-section of different embodiments of the rotatable ring, FIGS. 13-16 disclose different arrangements of the rotatable element, the first and the second part, FIGS. 17-20 disclose a radial cross-section of a part of the rotatable element and the first element, and FIGS. 21-29 disclose different embodiments of the rotatable element.

Figure 1:
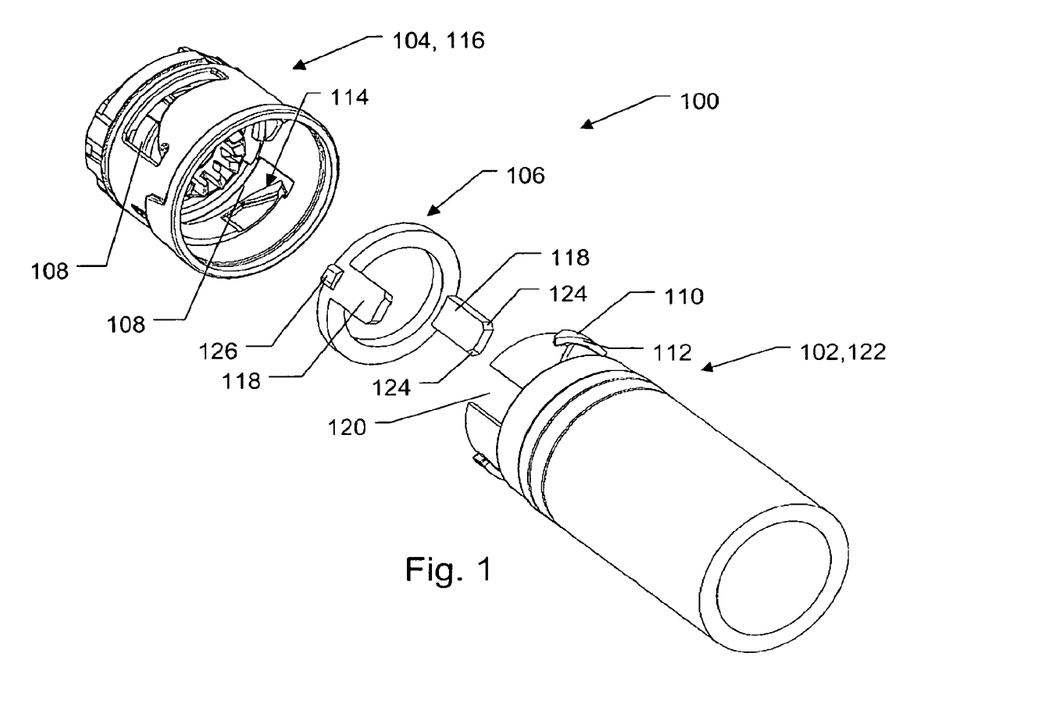
Figure 3:
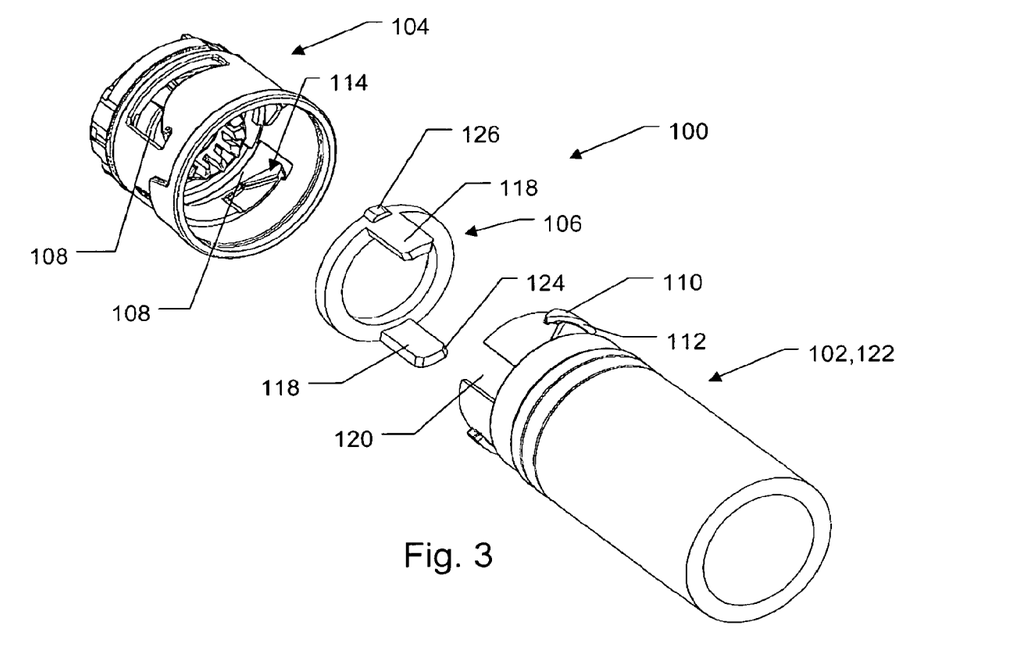
Figure 4:
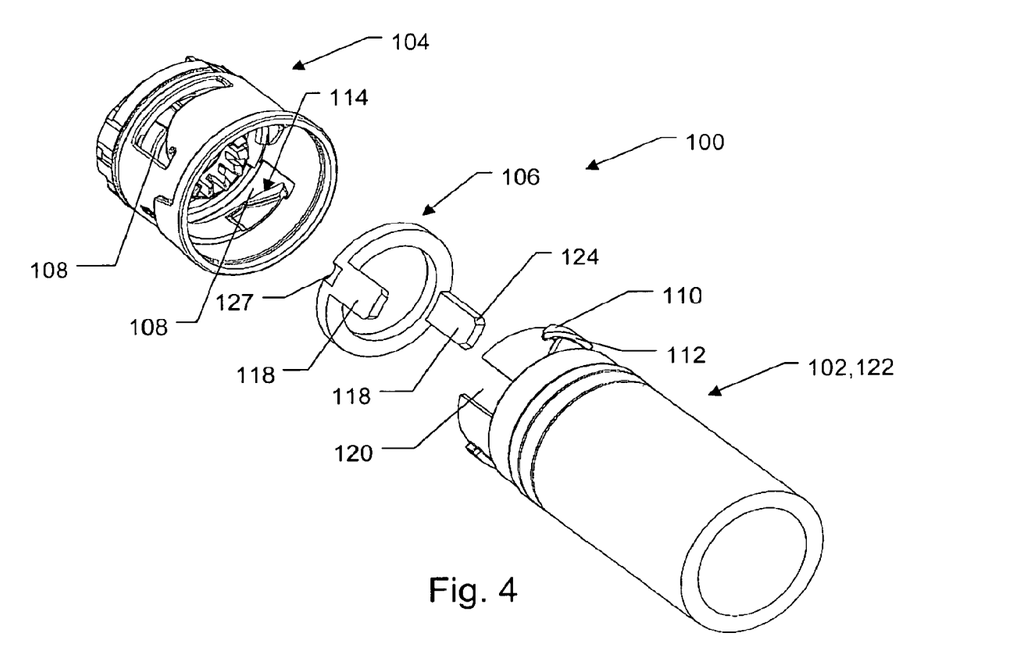

FIGS. 1, 3 and 4 discloses an exploded view of a medical delivery system 100 comprising a container 102, a dosing assembly 104 (of which only a part is disclosed for simplicity reasons) and a rotatable element 106. The dosing assembly 104 comprises a first fastening means 108 defining a groove for receiving a projection defined by a second fastening means 110. The container 102 may be fastened to the dosing assembly by advancing the projection into the groove whereby a distal facing surface 112 of the projection (the second fastening means 110) engages a proximal facing surface 114 of the groove (the first fastening means 108). Upon relative rotation between the dosing assembly 104 and the container 102 the two elements are pulled towards each other due to the engagement between the distal facing surface 112 and the proximal facing surface 114. The due to the angular extent of the groove the two elements are can only be rotated 30 degrees relative to each other i.e. less than one revolution.

Figure 5:
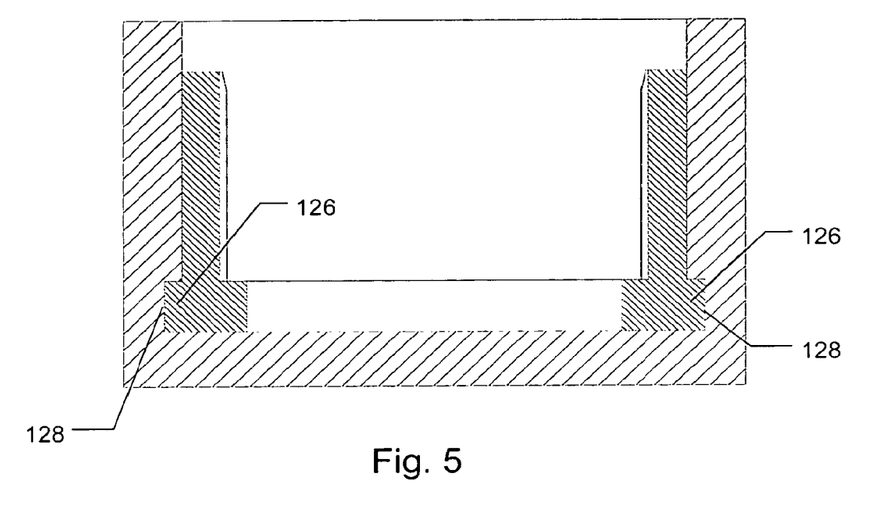
Figure 6:
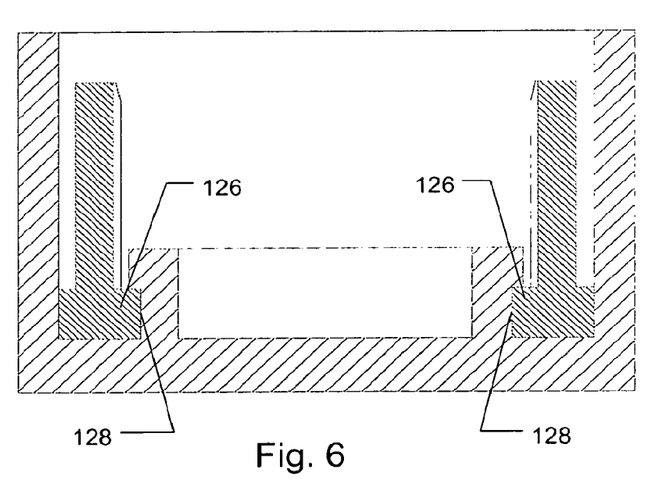
Figure 7:
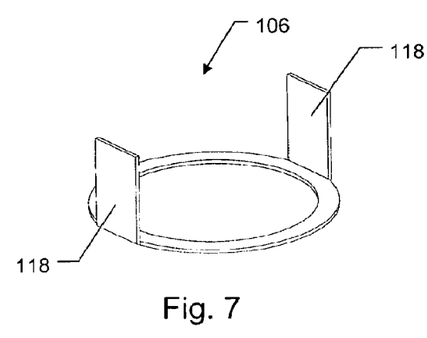
Figure 8:
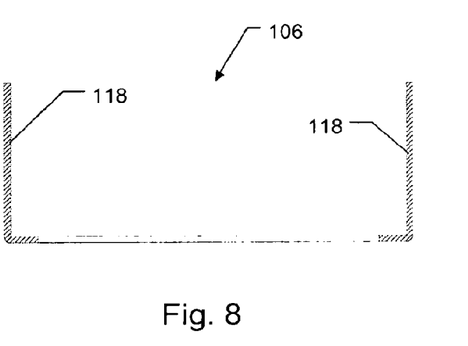

In FIGS. 1, 3 and 4 the first part 116 is defined by the dosing assembly 104, which, thus, comprises the rotatable element 106. When the two elements are assembled (as shown in FIGS. 5 and 6) the rotatable element may rotate relative to the first part 116 while being retained axially relative to the first part 116. The rotatable element 106 defines two protrusions 118 which are adapted to be received in indentations 120 defined in the container 102 which defines a second part 122. When the protrusions 118 are received in the indentations 120, the second part 122 and the rotatable element 106 are locked for relative rotational movement.

During fastening of the container to the dosing assembly the following occurs. The container is moved axially towards the dosing assembly. Subsequently the two elements are rotated relative to each other until the first and second fastening means (the projections and the groove) start to engage whereupon the protrusions start to be received in the indentations. Upon further relative rotation, the dosing assembly is moved towards the container, whereby the protrusions 118 are advanced further into the indentations 120. As the indentations rotate (due to the rotation of the container) the rotatable element 106 is caused to rotate relative to the dosing assembly.

Figure 2:
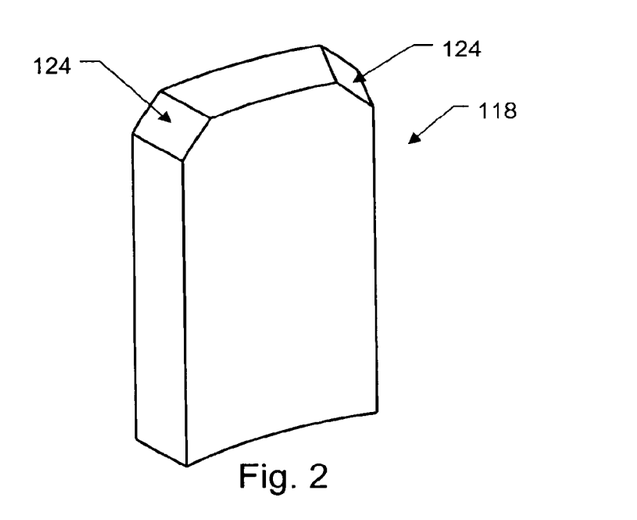

In order to ease receipt of the protrusions 118 in the indentations 120, the sidewalls of the protrusions 118 define inclined surfaces 124 (as shown in FIG. 2), whereby small angular inaccuracies in the relative position between the protrusions 118 and the indentations 120 still allow the protrusions 118 to be received in the indentations 120.

It will be appreciated that the relative rotational position between the first/second fastening means and the indentations/protrusions determines whether a predetermined container 102 may be attached to a predetermined dosing assembly 104. In FIG. 1 the protrusions will be received in the indentations upon further axial movement between the dosing assembly and the container. However, in FIG. 3 the indentations cannot be received in the protrusions due to their different rotational position.

When the dosing assembly and the rotatable element are assembled the rotatable element is temporarily retained rotationally relative to the dosing assembly by means of the knob 126 which engages corresponding knobs (not shown) in the dosing assembly, whereby the rotatable element may be retained in a predetermined number of positions. Alternatively, the rotatable element may be retained temporarily and relative to the dosing assembly due to notch 127 (shown in FIG. 4) which engages corresponding knobs of the dosing assembly.

According to an alternative embodiment (not shown), the rotatable element may be biased by a spring member towards a fixed rotational position relative to the first fastening means so that correct alignment between the rotatable element and the first fastening means will be automatically obtained, no matter whether the rotatable element has been tampered with. Such biasing means may be provided in addition to the above-mentioned knob 126 or notch 127.

The proximal surface part of the second fastening means 110 may be positioned at a distance $X_1$ from the extreme proximal part of the container 102. In some embodiments of the present invention, this distance $X_1$ is minimized, or ultimately, the proximal surface part of the second fastening means defines the proximal end of the container.

The axial extent of the male member forming the second fastening means 110 is defined by the parameter $t_1$.

In some embodiments, the axial length of the indentation 120 from the proximal end of the container 102 will be longer than $X_1+t_1$. Typically, an indentation length will be greater than the parameter $X_1+t_1$, such $X_1+t_1$ plus 50%, such as $X_1+t_1$ plus 100% such as $X_1+t_1$ plus 200%, such as $X_1+t_1$ plus 300%.

FIGS. 5 and 6 disclose a rotatable element which is retained axially relative to the dosing assembly by means of knobs 126 which engage tracks 128 of the dosing assembly.

Figure 9:
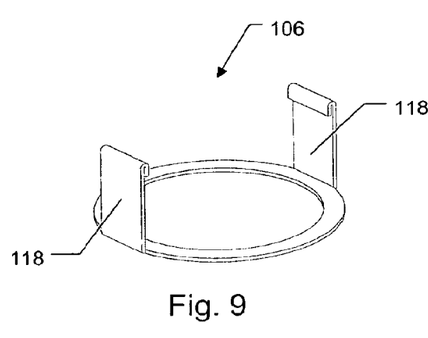
Figure 10:
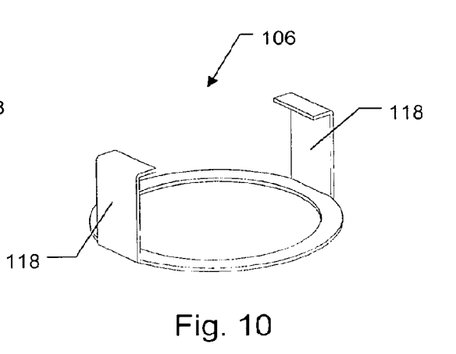
Figure 11:
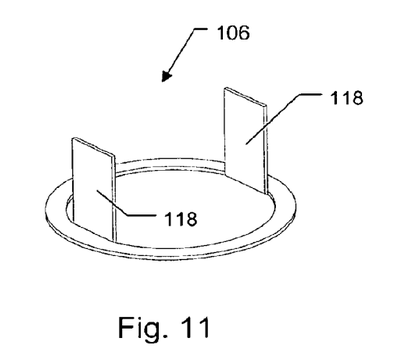
Figure 12:
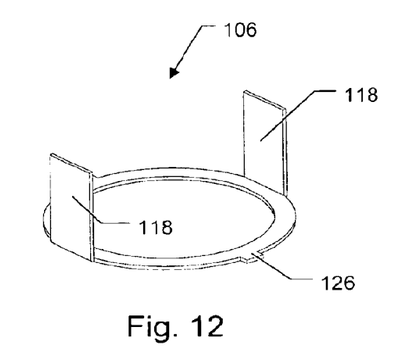

In order to provide a thin and rigid rotatable element, the rotatable element may be made from punched sheet metal which may be bent one or more times in order to provide the desired shape. FIGS. 7-12 discloses different shapes of the rotatable element. In FIGS. 9 and 10, sheet metal of the protrusions have been bent in order to increased the radial extent of the protrusions.

Figure 13:
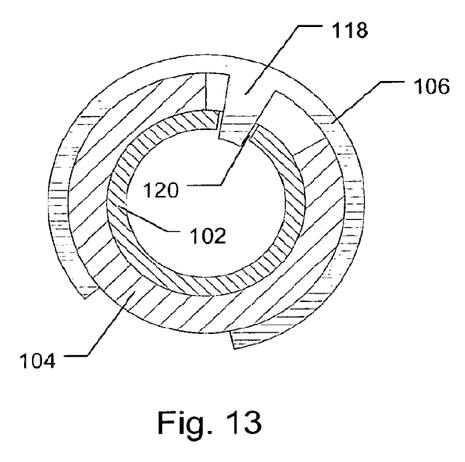

FIG. 13 discloses a radial cross-section through a dosing assembly 104, a container 102 and a rotatable element 106. The rotatable element 106 is provided on an outer surface of the dosing assembly 104 and protrusion 118 extend radially inward from an inner surface of the rotatable element 106. Upon axial advancement of the container towards the dosing assembly, the protrusion 118 is received in the indentation 120 of the container.

Figure 14:
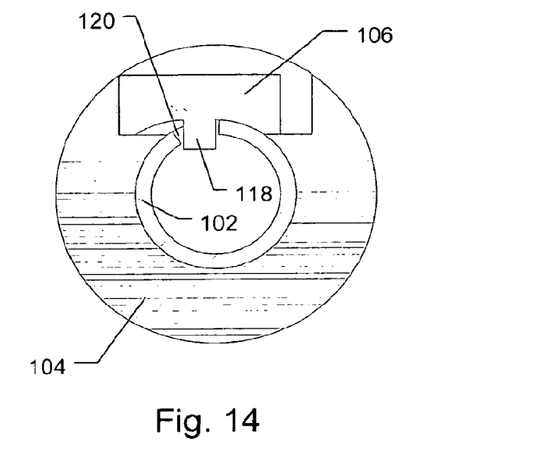
Figure 15:
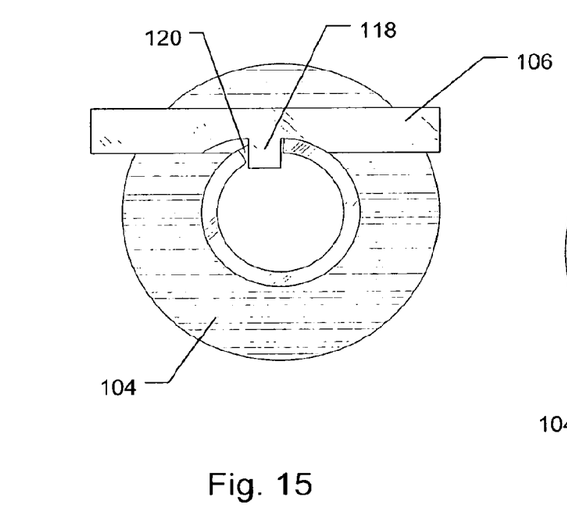
Figure 16:
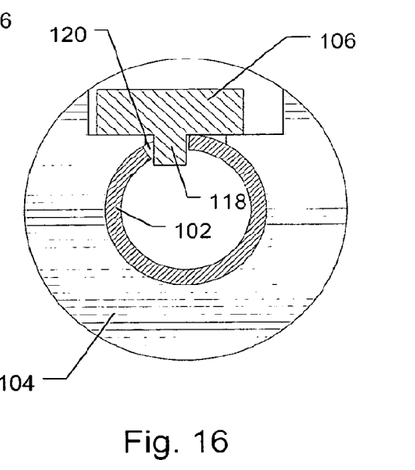

FIGS. 14-16 disclose embodiments of the rotatable element wherein the rotatable element is rotated and moved radially upon fastening of the container to the dosing assembly, whereby the rotatable element performs a linear movement when the container is fastened to the dosing assembly.

Figure 17:
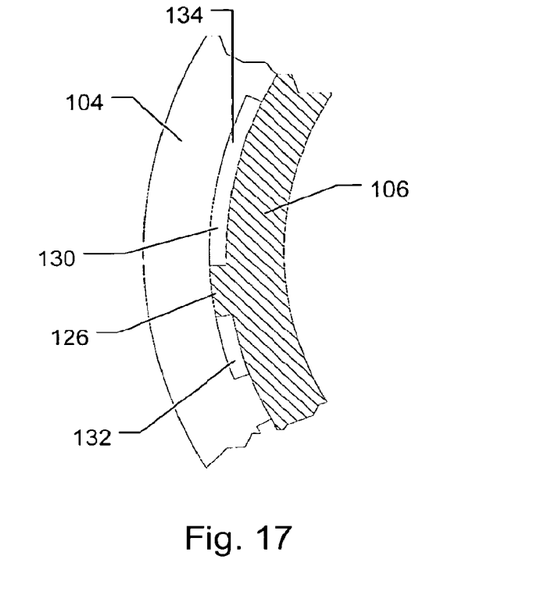
Figure 18:
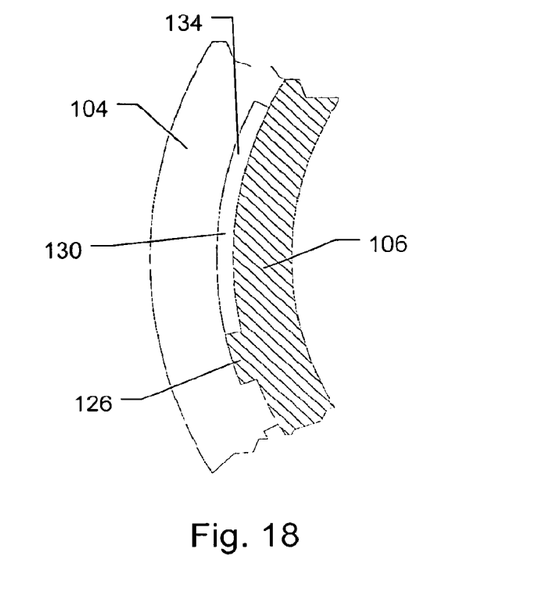

In FIGS. 17 and 18 the dosing assembly 104 defines circumferentially extending depression 130 in which knob 126 are received. Accordingly, the rotating element 106 can be changed between a first rotational position (disclosed in FIG. 18) wherein the knob 126 is positioned in a first end 132 of the depression 130, and a second rotational position (not shown) wherein the knob is positioned in the opposite second end 134 of the depression 130. In an alternative embodiment, the depression 130 is defined in the rotatable element and the knob is defined by the dosing assembly.

Figure 19:
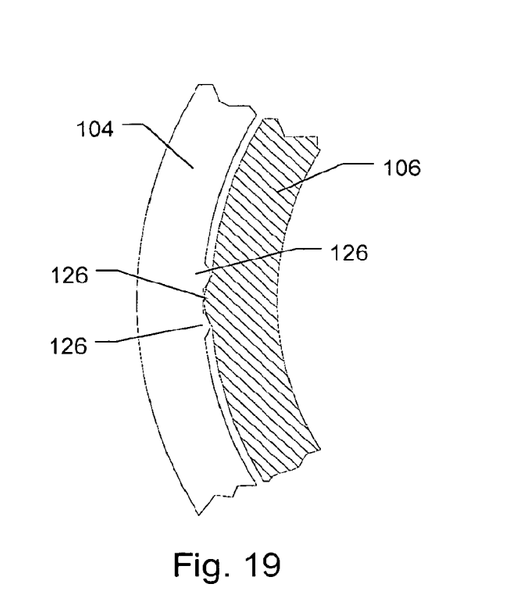
Figure 20:
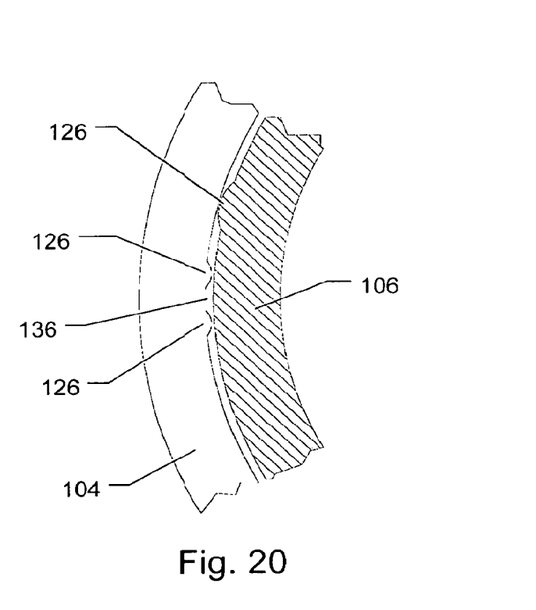
Figures 21, 22, 23, 24, 25:
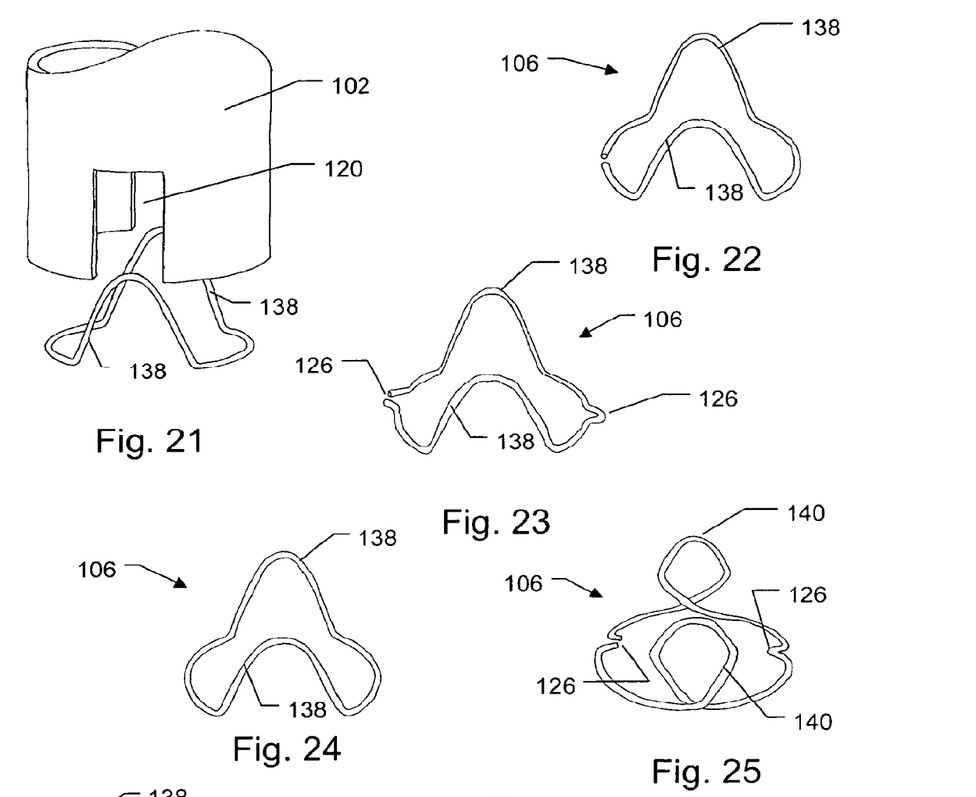
Figure 26:
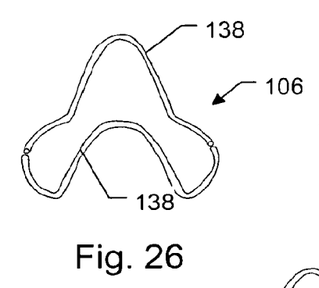

FIGS. 19 and 20 disclose a rotatable element 106 comprising a knob 126. Moreover, the dosing assembly 104 comprises a plurality of depressions 136 defined by knobs (in the figures only one depression is disclosed). The depressions 136 are spaced along inner sidewall of the dosing assembly whereby the rotatable element may be retained in a plurality of different rotational positions (corresponding in number to the number of depressions 136).

Figure 27:
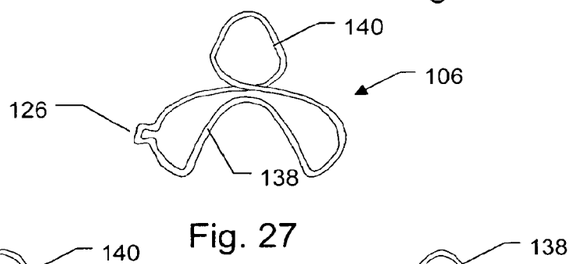
Figure 28:
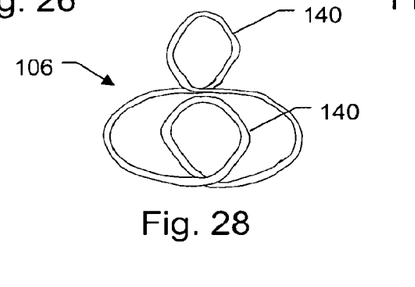
Figure 29:
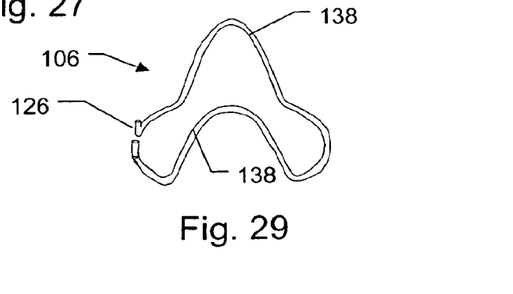

FIGS. 21-29 disclose embodiments of the rotatable element defining v-shaped protrusions 138 and/or loop-shaped protrusions 140. When the v-shaped protrusions 138 are advanced into the indentations 120 of the container 102, the distance between the widest parts of the v-shaped part decreases. Accordingly, ring-shaped elements defining two v-shaped protrusions 138 contracts upon advancement of the protrusions into the indentations. This is the case in FIGS. 22, 23, 24, 26 and 29. Similarly advancement of the loop-shaped protrusions 140 into the indentations 120 causes the ring-shaped element to expand when two loop-shaped protrusions are provided as disclosed in FIGS. 25 and 28. If the ring-shaped element comprises one v-shaped protrusion and one loop-shaped protrusion advancement of the protrusions into the indentations causes a radially extending knob 126 to rotate, as shown in FIG. 27. The ring-shaped element may be made in one piece wherein the ends of a wire or sheet metal are joint together as disclosed in FIGS. 21, 24 and 28. Alternatively, wire or sheet metal may be bent such that the ends abut each other or are provided adjacent each other as disclosed in FIGS. 22, 23, 25, 26 and 29. The ring shaped element may be made of one or two pieced of wire or sheet metal as disclosed in FIGS. 22 and 26 respectively.

The invention claimed is:

1. A medical delivery system comprising:
    a container adapted to contain a medicament in a chamber defined by the container and a slidably arranged piston which is moveable in a distal direction towards an outlet so as to reduce the volume of the chamber and expel the medicament through the outlet;
    a dosing assembly adapted to be fastened to the container, so as to allow a driver of the dosing assembly to move the piston of the container in the distal direction;
wherein the dosing assembly defines a first fastening structure which during fastening of the container to the dosing assembly engages a second fastening structure of the container whereby the container is fastened to the dosing assembly through a predetermined movement defined by at least one of the first and the second fastening structure, wherein at least a part of said predetermined movement is a concurrent axial and rotational movement, the predetermined movement being less than one revolution;
    wherein one of the container and the dosing assembly defines a first part comprising a rotatable element defining at least one protrusion and/or indentation which during fastening of the container to the dosing assembly are adapted to be received by/in one or more corresponding indentation or protrusion of a second part which is defined by the other one of the container and the dosing assembly,
    said rotatable element is adapted to rotate about a longitudinal axis of and relative to the first part during fastening of the container to the dosing assembly, the rotatable element being adapted to be retained in a predetermined angular position relative to the first part prior to fastening the container to the dosing assembly, and
    wherein the rotatable element comprises at least one radially extending knob which upon radial expansion of the rotatable element disengages a depression defined in a part fixedly arranged relative to the first fastening structure, whereby the rotatable element is unlocked relative to the first fastening structure and allowed to rotate about a center axis of and relative to the first fastening structure, and
    wherein the first and the second fastening structure the at least one protrusion and the at least one corresponding indentation are arranged such that the first and second fastening structure must at least partly engage in order for the one or more protrusions to be received in the one or more corresponding indentation(s).

2. A medical delivery system according to claim 1, wherein the rotatable element is locked for rotation relative to the container during fastening of the container to the dosing assembly.

3. A medical delivery system according to claim 1, wherein the rotatable element is locked for translational movement relative to the first part.

4. A medical delivery system according to claim 1, wherein the one or more protrusions and/or indentations extend in a substantially axial and/or radial direction of the device.

5. A medical delivery system according to claim 1, wherein the rotatable element is a ring-shaped element.

6. A medical delivery system according to claim 5, wherein the ring-shaped element comprises said at least one protrusion and is adapted to contract radially upon advancement of the at least one protrusion into the corresponding indentation of the second part.

7. A medical delivery system according to claim 6, wherein at least one protrusion of the ring-shaped element is v-shaped.

8. A medical delivery system according to claim 5, wherein the ring-shaped element comprises at least one protrusion and is adapted to expand radially upon advancement of each of the at least one protrusion into the corresponding indentation of the second part.

9. A medical delivery system according to claim 8, wherein at least one protrusion defines a loop.

10. A medical delivery system according to claim 1, wherein the rotatable element comprises at least one radially extending knob which upon radial contraction or expansion of the rotatable element disengages a depression defined in the first part, whereby the rotatable element is unlocked from the first part and allowed to rotate about a center axis of and relative to the first part.

11. A medical delivery system according to claim 1, wherein the rotatable element is adapted to be retained in a plurality of rotational positions relative to the first part.

12. A medical delivery system according to claim 1, wherein the container comprises a cartridge holder defining said second fastening structure, and a cartridge defining said chamber, and wherein the cartridge is non-detachably attached to the cartridge holder.

13. A medical delivery system comprising:
    a container adapted to contain a medicament in a chamber defined by the container and a slidably arranged piston which is moveable in a distal direction towards an outlet so as to reduce the volume of the chamber and expel the medicament through the outlet;

a dosing assembly adapted to be fastened to the container, so as to allow a driver of the dosing assembly to move the piston of the container in the distal direction;

wherein the dosing assembly defines a first fastening structure which during fastening of the container to the dosing assembly engages a second fastening structure of the container whereby the container is fastened to the dosing assembly through a predetermined movement defined by at least one of the first and the second fastening structure, the predetermined movement being less than one revolution;

wherein one of the container and the dosing assembly defines a first part comprising a rotatable element defining at least one protrusion and/or indentation which during fastening of the container to the dosing assembly are adapted to be received by/in one or more corresponding indentation or protrusion of a second part which is defined by the other one of the container and the dosing assembly, and     said rotatable element is adapted to rotate about a longitudinal axis of and relative to the first part during fastening of the container to the dosing assembly, the rotatable element being adapted to be retained in a predetermined angular position relative to the first part prior to fastening of the container to the dosing assembly, and     wherein the first and the second fastening structure the at least one protrusion and the at least one corresponding indentation are arranged such that the first and second fastening structure must at least partly engage in order for the one or more protrusions to be received in the at least one or more corresponding indentation(s), and     wherein at least a part of said predetermined movement is a concurrent axial and rotational movement, and wherein at least one of:

the first and second fastening structure, and the at least one protrusion and/or indentation of the rotatable element of the container, are adapted to prevent a part of the axial and/or rotational movement of the predetermined movement, so as to prevent coupling of the container to the dosing assembly, unless:

each of the first and second fastening structure defines a predetermined coding geometry,     each of the protrusion(s) of the rotatable element and/or indentation(s) of the container defines a predetermined coding geometry, and     the rotatable element is positioned in a predetermined angular position relative to the first fastening structure.

14. A medical delivery system according to claim 13, wherein the coding geometry of each of the first and/or second fastening structure, and each of the protrusion(s) of the rotatable element and/or indentation(s) of the container is defined by at least one of:

a circumferential extent of the first and second fastening structure,     an axial extent of the first and second fastening structure,     a radial extent of the first and second fastening structure and the circumferential position of the first and second fastening structure.

\* \* \* \* \*